(12) United States Patent
Hof et al.

(10) Patent No.: US 10,172,939 B2
(45) Date of Patent: *Jan. 8, 2019

(54) PHASE-CHANGE NANOPARTICLE (71) Applicant: NEW PHASE LTD., Petach Tikva (IL)

(72) Inventors: Raphael Hof, Kfar-Yona (IL); Raz Khandadash, Bat-Yam (IL); Ella Fremder, Haifa (IL)

(73) Assignee: NEW PHASE LTD., Givat Shmuel (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/852,293

(22) Filed: Dec. 22, 2017

(65) Prior Publication Data

US 2018/0117154 A1 May 3, 2018

Related U.S. Application Data

(63) Continuation of application No. 15/478,849, filed on Apr. 4, 2017, now Pat. No. 9,872,902, which is a
(Continued)

(51) Int. Cl.
*A61K 41/00* (2006.01)
*A61N 1/40* (2006.01)
(Continued)

(52) U.S. Cl.
CPC ............ *A61K 41/0052* (2013.01); *A61F 7/00* (2013.01); *A61K 47/06* (2013.01); *A61K 47/549* (2017.08);
(Continued)

(58) Field of Classification Search
CPC combination set(s) only.
See application file for complete search history.

(56) References Cited

U.S. PATENT DOCUMENTS 4,096,616 A 6/1978 Coffinberry
4,106,488 A 8/1978 Gordon
(Continued)

FOREIGN PATENT DOCUMENTS

CN 1724135 A 1/2006
CN 101836915 A 9/2010
(Continued)

OTHER PUBLICATIONS

Extended European Search Report of European Application No. 10811360.6 dated Mar. 20, 2013.
(Continued)

*Primary Examiner* — Joseph Stoklosa
*Assistant Examiner* — Adam Avigan
(74) *Attorney, Agent, or Firm* — Sughrue Mion, PLLC (57) ABSTRACT

Apparatus and methods are described for use with a subject suffering from cancer. A nanoparticle (22) includes an inner core (30) that comprises a phase-change material that is configured to absorb latent heat of fusion by undergoing a phase change. An outer layer (32) disposed around the inner core includes a plurality of nano-spheres (34) of at least one metal, and a plurality of molecules (38) of a substance that binds preferentially with cancerous cells relative to non-cancerous cells. The nanoparticle has a volume of at least 65,000 nm$^3$ and is elongatable into an ellipsoid, such that, when the nanoparticle is maximally elongated, each of the semi-axes defined by the ellipsoid is greater than 5 nm, and at least two of the semi axes of the ellipsoid are less than 30 nm. Other applications are also described.

30 Claims, 5 Drawing Sheets

Related U.S. Application Data continuation of application No. PCT/IL2015/051146, filed on Nov. 25, 2015.

(60) Provisional application No. 62/083,978, filed on Nov. 25, 2014.

(51) Int. Cl.
*A61F 7/00* (2006.01)
*A61K 47/06* (2006.01)
*A61K 47/69* (2017.01)
*A61K 47/60* (2017.01)
*A61K 47/54* (2017.01)

(52) U.S. Cl.
CPC .......... *A61K 47/60* (2017.08); *A61K 47/6929* (2017.08); *A61K 47/6935* (2017.08); *A61N 1/406* (2013.01)

(56) References Cited

U.S. PATENT DOCUMENTS

| | | | |
|---|---|---|---|
| 4,204,573 A | 5/1980 | Clark | |
| 4,392,040 A | 7/1983 | Rand et al. | |
| 4,440,217 A | 4/1984 | Stieler | |
| 4,569,836 A | 2/1986 | Gordon | |
| 4,678,460 A | 7/1987 | Rosner | |
| 4,747,826 A | 5/1988 | Sassano | |
| 4,983,159 A | 1/1991 | Rand | |
| 5,003,991 A | 4/1991 | Takayama et al. | |
| 5,217,363 A | 6/1993 | Brais et al. | |
| 5,317,506 A | 5/1994 | Coutre et al. | |
| 5,385,540 A | 1/1995 | Abbott et al. | |
| 5,545,210 A | 8/1996 | Hess et al. | |
| 5,658,234 A | 8/1997 | Dunlavy | |
| 5,667,522 A | 9/1997 | Flomenblit et al. | |
| 5,716,410 A | 2/1998 | Wang et al. | |
| 5,830,179 A | 11/1998 | Mikus et al. | |
| 5,964,744 A | 10/1999 | Balbierz et al. | |
| 5,984,893 A | 11/1999 | Ward | |
| 6,059,810 A | 5/2000 | Brown et al. | |
| 6,120,534 A | 9/2000 | Ruiz | |
| 6,323,459 B1 | 11/2001 | Maynard | |
| 6,390,185 B1 | 5/2002 | Proeschel | |
| 6,451,044 B1 | 9/2002 | Naghavi et al. | |
| 6,576,001 B2 | 6/2003 | Werneth et al. | |
| 6,746,439 B2 | 6/2004 | Lenker | |
| 6,768,921 B2 | 7/2004 | Organ et al. | |
| 6,805,711 B2 | 10/2004 | Quijano et al. | |
| 6,835,858 B1 | 12/2004 | De Jonge et al. | |
| 6,942,637 B2 | 9/2005 | Cartledge et al. | |
| 6,942,644 B2 | 9/2005 | Worthen | |
| 7,041,941 B2 | 5/2006 | Faries, Jr. et al. | |
| 7,074,175 B2 | 7/2006 | Handy et al. | |
| 7,112,273 B2 | 9/2006 | Weigel et al. | |
| 7,117,033 B2 | 10/2006 | Shalev et al. | |
| 7,120,489 B2 | 10/2006 | Shalev et al. | |
| 7,146,209 B2 | 12/2006 | Gross et al. | |
| 7,510,555 B2 | 3/2009 | Kanzius | |
| 7,560,160 B2 | 7/2009 | Sudarshan et al. | |
| 7,627,381 B2 | 12/2009 | Kanzius et al. | |
| 7,731,648 B2 | 6/2010 | Ivkov | |
| 7,919,184 B2 | 4/2011 | Mohapatra et al. | |
| 8,197,471 B1* | 6/2012 | Tersigni ............. | A61K 41/0052 606/27 |
| 8,463,397 B2 | 6/2013 | Munoz Marquez et al. | |
| 8,518,870 B2 | 8/2013 | Harrison, Jr. et al. | |
| 8,709,488 B2 | 4/2014 | Peyman | |
| 2002/0183829 A1 | 12/2002 | Doscher et al. | |
| 2004/0059385 A1 | 3/2004 | Yu | |
| 2004/0122494 A1 | 6/2004 | Eggers et al. | |
| 2004/0180086 A1 | 9/2004 | Ramtoola et al. | |
| 2004/0210269 A1 | 10/2004 | Shalev et al. | |
| 2004/0253304 A1 | 12/2004 | Gross et al. | |
| 2005/0033382 A1 | 2/2005 | Single | |
| 2005/0055082 A1 | 3/2005 | Ben Muvhar et al. | |
| 2005/0059928 A1 | 3/2005 | Larsson | |
| 2005/0074506 A1 | 4/2005 | Natan et al. | |
| 2005/0080351 A1 | 4/2005 | Larsson | |
| 2005/0090732 A1 | 4/2005 | Ivkov et al. | |
| 2005/0149170 A1 | 7/2005 | Tassel et al. | |
| 2005/0159790 A1 | 7/2005 | Shalev | |
| 2005/0202310 A1 | 9/2005 | Yahnker et al. | |
| 2005/0283327 A1 | 12/2005 | Bowman et al. | |
| 2005/0288777 A1 | 12/2005 | Rhee et al. | |
| 2006/0020299 A1 | 1/2006 | Shalev | |
| 2006/0074479 A1 | 4/2006 | Bailey et al. | |
| 2006/0083694 A1 | 4/2006 | Kodas et al. | |
| 2006/0194164 A1 | 8/2006 | Altshuler et al. | |
| 2006/0241747 A1 | 10/2006 | Shaoulian et al. | |
| 2006/0276882 A1 | 12/2006 | Case et al. | |
| 2007/0083245 A1 | 4/2007 | Lamensdorf et al. | |
| 2007/0154397 A1 | 7/2007 | Chang et al. | |
| 2007/0264481 A1 | 11/2007 | Desimone et al. | |
| 2008/0021537 A1 | 1/2008 | Ben-Muvhar et al. | |
| 2008/0033509 A1 | 2/2008 | Shalev et al. | |
| 2008/0167700 A1 | 7/2008 | Shalev et al. | |
| 2008/0172102 A1 | 7/2008 | Shalev | |
| 2008/0272331 A1* | 11/2008 | Mohapatra ............... | B01J 13/04 252/70 |
| 2009/0082832 A1 | 3/2009 | Carbunaru et al. | |
| 2010/0256708 A1 | 10/2010 | Thornton et al. | |
| 2011/0195526 A1 | 8/2011 | Su et al. | |
| 2012/0221081 A1 | 8/2012 | Hof et al. | |
| 2013/0078288 A1 | 3/2013 | Yu | |
| 2015/0112423 A1 | 4/2015 | Hof et al. | |
| 2015/0231282 A1* | 8/2015 | Pozzo .................. | A61K 49/226 424/9.5 |
| 2017/0209580 A1 | 7/2017 | Hof et al. | |

FOREIGN PATENT DOCUMENTS

| | | |
|---|---|---|
| DE | 197 45 890 C1 | 3/1999 |
| EP | 0 543 498 A1 | 5/1993 |
| JP | 3-178668 A | 12/1989 |
| WO | 94/01165 A1 | 1/1994 |
| WO | 97/26032 A1 | 7/1997 |
| WO | 00/66192 A1 | 11/2000 |
| WO | 02/00145 A1 | 1/2002 |
| WO | 03/028522 A2 | 4/2003 |
| WO | 03/105658 A2 | 12/2003 |
| WO | 2007/107762 A1 | 9/2007 |
| WO | 2008/148014 A2 | 12/2008 |
| WO | 2011/024159 A2 | 3/2011 |

OTHER PUBLICATIONS

Extended European Search Report of European Application No. 14192528.9 dated Jul. 9, 2015.
Extended European Search Report of European Application No. 14192528.9 dated Mar. 13, 2015.
Fluorodeoxyglucose, Wikipedia entry dated Jan. 18, 2009.
Huang Yong, et al. "Preparation and characterization of magnetic phase-change microcapsules", XP002693430, Database accession No. 11184663 (abstract), Jan. 2009.
International Preliminary Report on Patentability of International Application No. PCT/IL2010/000683, dated Feb. 28, 2012.
International Search Report of PCT/IL2015/051146, dated Mar. 18, 2016. [PCT/ISA/210].
J. Gordon Short, et al., "Physical Hyperthermia and Cancer Therapy", Proceedings of the IEEE, Jan. 1980, pp. 133-142, vol. 68, No. 1.
Jung-Whan Kim, et al., "Cancer's Molecular Sweet Tooth and the Warburg Effect", Cancer Res, Sep. 15, 2006, pp. 8927-8930, vol. 66, No. 18.
Luis F. Fajardo, MD, et al., "Effects of Hyperthermia in a Malignant Tumor", Cancer, 1980, pp. 613-623, vol. 45.
M. Johannsen, et al., "Clinical hyperthermia of prostate cancer using magnetic nanoparticles: Presentation of a new interstitial technique", Int. J. Hyperthermia, Nov. 2005, pp. 1-11.
Minghui Zhang, et al., "Encapsulated nano-heat-sinks for thermal management of heterogeneous chemical reactions", Nanoscale, The Royal Society of Chemistry, 2010, pp. 2790-2797, vol. 2, No. 12.

(56) References Cited

OTHER PUBLICATIONS

Mithun M. Shenoi, et al., "Nanoparticle Pre-Conditioning for Enhanced Thermal Therapies in Cancer", NIH Public Access, National Institute of Health, Nanomedicine (Lond) Apr. 2011, pp. 545-563, vol. 6, No. 3.

Notice of Reasons for Refusal for Japanese Patent Application No. 2012-526180, dated Apr. 8, 2014.

Notification of Defects in Israel Patent Application No. 218247 dated Jan. 4, 2015.

Office Action for U.S. Appl. No. 13/392,037 dated Apr. 8, 2015.

Office Action for U.S. Appl. No. 13/392,037, dated Aug. 19, 2014.

Office Action for U.S. Appl. No. 13/392,037, dated Dec. 11, 2015.

Office Action for U.S. Appl. No. 13/392,037, dated May 16, 2016.

Peter Degn, et al., "Lipase-catalysed synthesis of glucose fatty acid esters in tert-butanol", Biotechnology Letters, 1999, pp. 275-280, vol. 21.

Peter Degn, et al., "Optimization of Carbohydrate Fatty Acid Ester Synthesis in Organic Media by a Lipase from Candida antarctica", Biotechnology and Bioengineering, Sep. 20, 2001, pp. 483-491, vol. 74, No. 6.

Robby A. Petros, et al., "Strategies in the design of nanoparticles for therapeutic applications", Nature Reviews, Drug Discovery, Aug. 2010, pp. 615-627, vol. 9.

Sharon Thomsen, et al., "Pathologic Analysis of Photothermal and Photomechanical Effects of Laser-Tissue Interactions", Photochemistry and Photobiology, 1991, pp. 825-835, vol. 53, No. 6.

U.S. Appl. No. 61/275,068, filed Aug. 24, 2009.
U.S. Appl. No. 61/275,071, filed Aug. 24, 2009.
U.S. Appl. No. 61/275,089, filed Aug. 24, 2009.
U.S. Appl. No. 62/083,978, filed Nov. 25, 2014.

Wim H. De Jong, et al., "Particle size-dependent organ distribution of gold nanoparticles after intravenous administration", ElSevier, Science Direct, Biomaterials, 2008, pp. 1912-1919, vol. 29.

Written Opinion of PCT/IL2010/000683, dated Feb. 18, 2011.

Written Opinion of PCT/IL2015/051146, dated Mar. 18, 2016. [PCT/ISA/237].

"Cryotherapy: A Novel Treatment Option for Prostate Cancer", dated Aug. 12, 2008, www.galilmedical.com.

Belen Zalba, et al., "Review on thermal energy storage with phase change: materials, heat transfer analysis and applications", Science Direct, Applied Thermal Engineering, 2003, pp. 251-283, vol. 23.

Changhong Liu, et al., "Energy Absorption of Gold Nanoshells in Hyperthermia Therapy", IEEE Transactions on Nanobioscience, Sep. 2008, pp. 206-214, vol. 7, No. 3.

Yonggang LV, et al., "Theoretical model for thermal protection by microencapsulated phase change micro/nanoparticles during hyperthermia", Heat Mass Transfer, 2012, pp. 573-584, vol. 48.

Notice of Allowance dated Sep. 18, 2017 in U.S. Appl. No. 15/478,849.

"Golden slingshot", The Economist, Nov. 6, 2008.

An Office Action dated Apr. 6, 2018, which issued during the prosecution of U.S. Appl. No. 14/579,340.

\* cited by examiner

PHASE-CHANGE NANOPARTICLE

CROSS REFERENCES TO RELATED APPLICATIONS

The present application is a continuation of U.S. Ser. No. 15/478,849 to Hof, filed Apr. 4, 2017 (published as US 2017/0209580; issued as U.S. Pat. No. 9,872,902), which is a continuation of PCT Application no. PCT/IL2015/051146 to Hof, entitled "Phase-change nanoparticle," filed Nov. 25, 2015 (published as WO 16/084082), which claims priority from U.S. Provisional Application 62/083,978 to Hof, entitled "Phase-change nanoparticle," filed Nov. 25, 2014.

The present application is related to U.S. Ser. No. 13/392,037 (issued as U.S. Pat. No. 9,572,695) to Hof, which is the US National Phase of International Patent Application PCT/IL2010/000683 (published as WO 11/024,159) to Hof, entitled "Phase-change and shape-change materials, filed Aug. 22, 2010, which claims priority from:

U.S. Provisional Patent Application 61/275,068 to Hof, entitled "Phase change implant," filed Aug. 24, 2009;

U.S. Provisional Patent Application 61/275,071 to Hof, entitled "Shape and function change of implanted element," filed Aug. 24, 2009;

U.S. Provisional Patent Application 61/275,089 to Hof, entitled "Phase change materials for treating cancer," filed Aug. 24, 2009.

All of the above-referenced applications are incorporated herein by reference.

FIELD OF EMBODIMENTS OF THE INVENTION

Some applications of the present invention generally relate to implanted medical apparatus. Specifically, some applications of the present invention relate to the use of phase-change materials.

BACKGROUND

Hyperthermia is a method of treating cancer, in which heat is applied to tissue of the cancer patient, in order to kill cancer cells within the tissue. Hyperthermia is typically used to treat cancer patients in combination with other therapies, such as radiotherapy and chemotherapy.

The Warburg effect describes the observation that most cancer cells predominantly produce energy by glycolysis followed by lactic acid fermentation, rather than by oxidation of pyruvate like most healthy cells. The Warburg effect results in cancer cells consuming more than 20 times the quantity of glucose to produce energy than do healthy cells, ceteris paribus.

When a solid material is heated until its melting point, the material undergoes a phase-change to its liquid state. During the phase-change, the material accumulates a certain amount of heat, which is called the latent heat of fusion, or the enthalpy change of fusion. The temperature of the material stays relatively constant when the phase change occurs.

SUMMARY OF EMBODIMENTS

In accordance with some applications of the present invention, a plurality of nanoparticles are administered to a subject who is suffering from cancer. The nanoparticles typically have the following characteristics:

(1) The nanoparticles preferentially bind to cancerous cells relative to healthy cells.

(2) The nanoparticles preferentially absorb energy transmitted toward the subject's body relative to absorption of the energy by tissue of the subject.

(3) The nanoparticles prevent healthy tissue surrounding the cancerous cells from being heated to a temperature that is greater than a given temperature.

(4) The nanoparticles are at least partially self-adjusting in shape, the nanoparticles being configured to be elongatable to an ellipsoid shape such as to pass through a gap in an anatomical barrier that has a size that is greater than a minimum threshold size, for example, in response to osmotic and/or hydrostatic pressure being exerted on the nanoparticles.

It is noted that typically, the nanoparticles will not become elongated to a precise geometric ellipsoid shape, but will assume a generally ellipsoidal shape when maximally elongated.

A heating device is typically used in conjunction with the administration of the nanoparticles to the subject. The heating device acts as an energy transmission unit that transmits energy toward the subject's body, causing at least some of the cancerous cells to become heated, such that the heated cells become injured, or ruptured, leading to cell death.

There is therefore provided, in accordance with some applications of the present invention, apparatus for use with a subject suffering from cancer, a body of the subject containing cancerous cells and non-cancerous cells, and for use with a heating device configured to heat at least a portion of the subject's body, the apparatus including:

a nanoparticle including:
  an inner core that includes a phase-change material that is configured to absorb latent heat of fusion by undergoing a phase change selected from the group consisting of: solid to liquid, and gel to liquid, the phase-change occurring at a phase-change temperature of between 42° C. and 80° C.;
  an outer layer disposed around the inner core, the outer layer including:
    a plurality of nano-spheres of at least one metal; and
    a plurality of molecules of a substance that binds preferentially with cancerous cells relative to non-cancerous cells,
  the nanoparticle having a volume of at least 65,000 nm$^3$,
  the nanoparticle being elongatable into an ellipsoid, such that when the nanoparticle is maximally elongated:
    each of the semi-axes defined by the ellipsoid is greater than 5 nm, and
    at least two of the semi axes of the ellipsoid are less than 30 nm.

For some applications, the phase-change material is configured to undergo the selected phase change at a phase-change temperature of between 42° C. and 50° C.

For some applications, the phase-change material is configured to undergo the selected phase change at a phase-change temperature of between 50° C. and 60° C.

For some applications, the phase-change material is configured to undergo the selected phase change at a phase-change temperature of between 60° C. and 80° C.

For some applications, the nanoparticle is configured to become elongated in response to hydrostatic pressure within the subject's body.

For some applications, the nanoparticle is configured to become elongated in response to osmotic pressure within the subject's body.

For some applications, the nanoparticle is configured to be blocked from passing through a blood brain barrier of the subject, by being elongatable into an ellipsoid, such that even when the nanoparticle is maximally elongated, each of the semi-axes defined by the ellipsoid is greater than 5 nm.

For some applications, the nanoparticle is configured to be able to pass through a liver of the subject, by being elongatable into an ellipsoid, such that when the nanoparticle is maximally elongated at least two of the semi axes of the ellipsoid are less than 30 nm.

For some applications, the nanoparticle is configured to be able to pass through glands of the subject, by being elongatable into an ellipsoid, such that when the nanoparticle is maximally elongated at least two of the semi axes of the ellipsoid are less than 30 nm.

For some applications, the nanoparticle is configured to be able to pass through a mononuclear phagocyte system of the subject, by being elongatable into an ellipsoid, such that when the nanoparticle is maximally elongated at least two of the semi axes of the ellipsoid are less than 30 nm.

For some applications, the nanoparticle is configured to be able to pass through a spleen of the subject, by being elongatable into an ellipsoid, such that when the nanoparticle is maximally elongated at least two of the semi axes of the ellipsoid are less than 30 nm.

For some applications, the phase-change material is configured to prevent the nanoparticle from being heated to a temperature that is greater than the phase change temperature, by absorbing latent heat of fusion.

For some applications, the nanoparticle is elongatable into an ellipsoid, such that when the nanoparticle is maximally elongated each of the semi-axes defined by the ellipsoid is greater than 10 nm.

For some applications, the nanoparticle is elongatable into an ellipsoid, such that when the nanoparticle is maximally elongated at least two of the semi axes of the ellipsoid are less than 25 nm.

For some applications, the nano-spheres of the at least one metal are configured to cause the nanoparticle to preferentially absorb energy from the heating device relative to tissue of the subject.

For some applications, the nano-spheres of the at least one metal include gold nano-spheres.

For some applications, the plurality of molecules of the substance that binds preferentially with cancerous cells relative to non-cancerous cells include a plurality of glucose molecules.

For some applications, the plurality of molecules of the substance that binds preferentially with cancerous cells relative to non-cancerous cells include a plurality of molecules of a glucose derivative.

For some applications, the plurality of molecules of the substance that binds preferentially with cancerous cells relative to non-cancerous cells include a plurality of molecules of a glucose analog.

For some applications, the plurality of molecules of the substance that binds preferentially with cancerous cells relative to non-cancerous cells include a plurality of molecules of an antibody.

For some applications, the nanoparticle further includes a plurality of polymer chains disposed between the inner core and the outer layer, the outer layer being bound to the inner core via the polymer chains.

For some applications, the polymer chains include chains of a polyetheramine.

For some applications, the nanoparticle further includes a plurality of polymer chains disposed around the outer layer.

For some applications, the polymer chains include chains of a polyetheramine.

For some applications, the polymer chains are configured to at least partially mask at least the outer layer from phagocytic cells of a mononuclear phagocyte system of the subject.

For some applications, the nanoparticles are configured to be used with an inductive radiofrequency heating device, and the nano-spheres are configured to be heated by the inductive radiofrequency heating device.

For some applications, the nanoparticles are configured to be used with an inductive radiofrequency heating device that transmits RF energy at a given frequency, and the nano-spheres have a resonant frequency that matches the given frequency.

For some applications, each of the nano-spheres has a diameter that is between 1 nm and 10 nm.

For some applications, each of the nano-spheres has a diameter that is between 3 nm and 7 nm.

For some applications, each of the nano-spheres is separated from all others of the nano-spheres of the outer layer by a minimum separation of between 0.3 nm and 2 nm.

For some applications, each of the nano-spheres is separated from all others of the nano-spheres of the outer layer by a minimum separation of between 0.5 nm and 1.5 nm.

For some applications, the inner core has a volume of 50,000-270,000 nm$^3$.

For some applications, the inner core has a volume of 85,000-145,000 nm$^3$.

For some applications, the nanoparticle has a volume of 110,000-700,000 nm$^3$.

For some applications, the nanoparticle has a volume of 180,000-525,000 nm$^3$.

For some applications, the phase-change material includes an organic phase-change material.

For some applications, the phase-change material includes paraffin.

There is further provided, in accordance with some applications of the present invention, a method for use with a subject suffering from cancer, a body of the subject containing cancerous cells and non-cancerous cells, the method including:

providing a plurality of nanoparticles, each of the nanoparticles including:
  an inner core that includes a phase-change material that is configured to absorb latent heat of fusion, by undergoing a phase change selected from the group consisting of: solid to liquid, and gel to liquid, the phase-change occurring at a phase-change temperature of between 42° C. and 80° C.,
  an outer layer disposed around the inner core, the outer layer including:
    a plurality of nano-spheres of at least one metal, and
    a plurality of molecules of a substance that binds preferentially with cancerous cells relative to non-cancerous cells,
  the nanoparticle having a volume of at least 65,000 nm3,
  each of the nanoparticles being elongatable into an ellipsoid, such that when the nanoparticle is maximally elongated:
    each of the semi-axes defined by the ellipsoid is greater than 5 nm, and
    at least two of the semi axes of the ellipsoid are less than 30 nm; and administering the plurality of nanoparticles to the subject.

For some applications, the method further includes, subsequent to administering the plurality of nanoparticles to the subject, heating at least a portion of the subject's body to the phase-change temperature of the phase-change material, using a heating device.

For some applications, administering the plurality of nanoparticles to the subject includes administering the plurality of nanoparticles to the subject, the nanoparticles being configured to become elongated in response to hydrostatic pressure within the subject's body.

For some applications, administering the plurality of nanoparticles to the subject includes administering the plurality of nanoparticles to the subject, the nanoparticles being configured to become elongated in response to osmotic pressure within the subject's body.

For some applications, administering the plurality of nanoparticles to the subject includes preventing the nanoparticles from passing through a blood brain barrier of the subject, due to each of the nanoparticles being elongatable into an ellipsoid, such that even when the nanoparticle is maximally elongated, each of the semi-axes defined by the ellipsoid is greater than 5 nm.

For some applications, administering the plurality of nanoparticles to the subject includes facilitating the nanoparticles passing through glands of the subject, due to each of the nanoparticles being elongatable into an ellipsoid, such that when the nanoparticle is maximally elongated at least two of the semi axes of the ellipsoid are less than 30 nm.

For some applications, administering the plurality of nanoparticles to the subject includes facilitating the nanoparticles passing through a mononuclear phagocyte system of the subject, due to each of the nanoparticles being elongatable into an ellipsoid, such that when the nanoparticle is maximally elongated at least two of the semi axes of the ellipsoid are less than 30 nm.

For some applications, administering the plurality of nanoparticles to the subject includes facilitating the nanoparticles passing through a liver of the subject, due to each of the nanoparticles being elongatable into an ellipsoid, such that when the nanoparticle is maximally elongated at least two of the semi axes of the ellipsoid are less than 30 nm.

For some applications, administering the plurality of nanoparticles to the subject includes facilitating the nanoparticles passing through a spleen of the subject, due to each of the nanoparticles being elongatable into an ellipsoid, such that when the nanoparticle is maximally elongated at least two of the semi axes of the ellipsoid are less than 30 nm.

For some applications, administering the plurality of nanoparticles to the subject includes administering a plurality of nanoparticles to the subject, each of the nanoparticles being elongatable into an ellipsoid, such that when the nanoparticle is maximally elongated at least two of the semi axes of the ellipsoid are less than 25 nm.

For some applications, administering the plurality of nanoparticles to the subject includes administering a plurality of nanoparticles to the subject, each of the nanoparticles being elongatable into an ellipsoid, such that when the nanoparticle is maximally elongated each of the semi-axes defined by the ellipsoid is greater than 10 nm.

For some applications, administering the plurality of nanoparticles to the subject includes administering the plurality of nanoparticles to the subject, the nano-spheres of the metal of the outer layer of the nanoparticles including gold nano-spheres.

For some applications, administering the plurality of nanoparticles to the subject includes administering the plurality of nanoparticles to the subject, the substance that binds preferentially with cancerous cells relative to non-cancerous cells including glucose.

For some applications, administering the plurality of nanoparticles to the subject includes administering the plurality of nanoparticles to the subject, the substance that binds preferentially with cancerous cells relative to non-cancerous cells including a glucose derivative.

For some applications, administering the plurality of nanoparticles to the subject includes administering the plurality of nanoparticles to the subject, the substance that binds preferentially with cancerous cells relative to non-cancerous cells including a glucose analog.

For some applications, administering the plurality of nanoparticles to the subject includes administering the plurality of nanoparticles to the subject, the substance that binds preferentially with cancerous cells relative to non-cancerous cells including an antibody.

For some applications, administering the plurality of nanoparticles to the subject includes preventing the nanoparticles from being heated to a temperature that is greater than the phase change temperature, in response to the heating of the portion of the subject's body, due to the phase-change material of the inner core of the nanoparticles absorbing latent heat of fusion.

For some applications, administering the plurality of nanoparticles to the subject includes causing the nanoparticles to preferentially absorb energy from the heating device relative to tissue of the subject, due to the nano-spheres of the metal absorbing energy from the heating device.

For some applications:
administering the plurality of nanoparticles to the subject includes administering the plurality of nanoparticles to the subject, the phase-change material of each of the nanoparticles having a phase-change temperature of between 42° C. and 50° C.; and
heating at least the portion of the subject's body to the phase-change temperature of the phase-change material includes heating at least the portion of the subject's body to a temperature of between 42° C. and 50° C.

For some applications:
administering the plurality of nanoparticles to the subject includes administering the plurality of nanoparticles to the subject, the phase-change material of each of the nanoparticles having a phase-change temperature of between 50° C. and 60° C.; and
heating at least the portion of the subject's body to the phase-change temperature of the phase-change material includes heating at least the portion of the subject's body to a temperature of between 50° C. and 60° C.

For some applications:
administering the plurality of nanoparticles to the subject includes administering the plurality of nanoparticles to the subject, the phase-change material of each of the nanoparticles having a phase-change temperature of between 60° C. and 80° C.; and
heating at least the portion of the subject's body to the phase-change temperature of the phase-change material includes heating at least the portion of the subject's body to a temperature of between 60° C. and 80° C.

For some applications, administering the plurality of nanoparticles to the subject includes administering the plurality of nanoparticles to the subject, each of the nanoparticles including a plurality of polymer chains disposed between the inner core and the outer layer, the outer layer being bound to the inner core via the polymer chains.

For some applications, administering the plurality of nanoparticles to the subject includes administering the plurality of nanoparticles to the subject, the polymer chains of each of the nanoparticles including chains of a polyetheramine.

For some applications, administering the plurality of nanoparticles to the subject includes administering the plurality of nanoparticles to the subject, each of the nanoparticles including a plurality of polymer chains disposed around its outer layer.

For some applications, administering the plurality of nanoparticles to the subject includes administering the plurality of nanoparticles to the subject, the polymer chains of each of the nanoparticles including chains of a polyetheramine.

For some applications, administering the plurality of nanoparticles to the subject includes at least partially masking at least the outer layer of the nanoparticles from phagocytic cells of a mononuclear phagocyte system of the subject, due to the polymer chains disposed around the outer layer of each of the nanoparticles.

For some applications, heating the portion of the subject's body includes heating the portion of the subject's body by directing inductive radiofrequency heating toward the nano-spheres.

For some applications, directing inductive the radiofrequency heating toward the nano-spheres includes transmitting RF energy at a given frequency, the nano-spheres having a resonant frequency that matches the given frequency.

For some applications, administering the plurality of nanoparticles to the subject includes administering the plurality of nanoparticles to the subject, each of the nano-spheres of each of the nanoparticles having a diameter that is between 1 nm and 10 nm.

For some applications, administering the plurality of nanoparticles to the subject includes administering the plurality of nanoparticles to the subject, each of the nano-spheres of each of the nanoparticles having a diameter that is between 3 nm and 7 nm.

For some applications, administering the plurality of nanoparticles to the subject includes administering the plurality of nanoparticles to the subject, each of the nano-spheres of each of the nanoparticles being separated from all others of the nano-spheres of the outer layer of the nanoparticle by a minimum separation of between 0.3 nm and 2 nm.

For some applications, administering the plurality of nanoparticles to the subject includes administering the plurality of nanoparticles to the subject, each of the nano-spheres of each of the nanoparticles being separated from all others of the nano-spheres of the outer layer of the nanoparticle by a minimum separation of between 0.5 nm and 1.5 nm.

For some applications, administering the plurality of nanoparticles to the subject includes administering the plurality of nanoparticles to the subject, the inner core of each of the nanoparticles having a volume of 50,000-270,000 $nm^3$.

For some applications, administering the plurality of nanoparticles to the subject includes administering the plurality of nanoparticles to the subject, the inner core of each of the nanoparticles having a volume of 85,000-145,000 $nm^3$.

For some applications, administering the plurality of nanoparticles to the subject includes administering the plurality of nanoparticles to the subject, each of the nanoparticles having a volume of 110,000-700,000 $nm^3$.

For some applications, administering the plurality of nanoparticles to the subject includes administering the plurality of nanoparticles to the subject, each of the nanoparticles having a volume of 180,000-525,000 $nm^3$.

For some applications, administering the plurality of nanoparticles to the subject includes administering the plurality of nanoparticles to the subject, the phase-change material of the inner core of the nanoparticles including an organic phase-change material.

For some applications, administering the plurality of nanoparticles to the subject includes administering the plurality of nanoparticles to the subject, the phase-change material of the inner core of the nanoparticles including paraffin.

There is additionally provided, in accordance with some applications of the present invention, a method including:
synthesizing a nanoparticle to have a volume of at least 65,000 nm3, and to be elongatable into an ellipsoid, such that when the nanoparticle is maximally elongated:
each of the semi-axes defined by the ellipsoid is greater than 5 nm, and
at least two of the semi axes of the ellipsoid are less than 30 nm, the synthesizing being performed by:
providing an inner core that includes a phase-change material that is configured to absorb latent heat of fusion, by undergoing a phase change selected from the group consisting of: solid to liquid, and gel to liquid, the phase-change occurring at a phase-change temperature of between 42° C. and 80° C.,
binding an outer layer to the inner core, the outer layer including:
a plurality of nano-spheres of at least one metal, and
a plurality of molecules of a substance that binds preferentially with cancerous cells relative to non-cancerous cells.

For some applications, providing the inner core includes providing the inner core, the phase-change material of the inner core having a phase-change temperature of between 42° C. and 50° C.

For some applications, providing the inner core includes providing the inner core, the phase-change material of the inner core having a phase-change temperature of between 50° C. and 60° C.

For some applications, providing the inner core includes providing the inner core, the phase-change material of the inner core having a phase-change temperature of between 60° C. and 80° C.

For some applications, synthesizing the nanoparticle includes synthesizing the nanoparticle to be elongatable in response to hydrostatic pressure.

For some applications, synthesizing the nanoparticle includes synthesizing the nanoparticle to be elongatable in response to osmotic pressure.

For some applications, synthesizing the nanoparticle includes synthesizing the nanoparticle to be elongatable into an ellipsoid, such that when the nanoparticle is maximally elongated each of the semi-axes defined by the ellipsoid is greater than 10 nm.

For some applications, synthesizing the nanoparticle includes synthesizing the nanoparticle to be elongatable into an ellipsoid, such that when the nanoparticle is maximally elongated at least two of the semi axes of the ellipsoid are less than 25 nm.

For some applications, binding the outer layer to the inner core includes binding an outer layer to the inner core, the outer layer including a plurality of gold nano-spheres.

For some applications, binding the outer layer to the inner core includes binding the outer layer to the inner core, the substance that binds preferentially with cancerous cells relative to non-cancerous cells including glucose.

For some applications, binding the outer layer to the inner core includes binding the outer layer to the inner core, the substance that binds preferentially with cancerous cells relative to non-cancerous cells including a glucose derivative.

For some applications, binding the outer layer to the inner core includes binding the outer layer to the inner core, the substance that binds preferentially with cancerous cells relative to non-cancerous cells including a glucose analog.

For some applications, binding the outer layer to the inner core includes binding the outer layer to the inner core, the substance that binds preferentially with cancerous cells relative to non-cancerous cells including an antibody.

For some applications, binding the outer layer to the inner core includes binding the outer layer to the inner core via a plurality of polymer chains.

For some applications, binding the outer layer to the inner core includes binding the outer layer to the inner core via a plurality of chains of a polyetheramine.

For some applications, synthesizing the nanoparticle includes binding a plurality of polymer chains to the outer layer, such that the polymer chains are disposed around the outer layer.

For some applications, binding the plurality of polymer chains to the outer layer includes binding a plurality of chains of a polyetheramine polymer to the outer layer.

For some applications, binding the outer layer to the inner core includes binding an outer layer to the inner core, each of the nano-spheres of the outer layer having a diameter that is between 1 nm and 10 nm.

For some applications, binding the outer layer to the inner core includes binding an outer layer to the inner core, each of the nano-spheres of the outer layer having a diameter that is between 3 nm and 7 nm.

For some applications, binding the outer layer to the inner core includes binding an outer layer to the inner core, each of the nano-spheres of the outer layer being separated from all others of the nano-spheres of the outer layer by a minimum separation of between 0.3 nm and 2 nm.

For some applications, binding the outer layer to the inner core includes binding an outer layer to the inner core, each of the nano-spheres of the outer layer being separated from all others of the nano-spheres of the outer layer by a minimum separation of between 0.5 nm and 1.5 nm.

For some applications, providing the inner core that includes the phase-change material includes providing an inner core having a volume of 50,000-270,000 nm$^3$.

For some applications, providing the inner core that includes the phase-change material includes providing an inner core having a volume of 85,000-145,000 nm$^3$.

For some applications, synthesizing the nanoparticle includes synthesizing the nanoparticle to have a volume of 110,000-700,000 nm$^3$.

For some applications, synthesizing the nanoparticle includes synthesizing the nanoparticle to have a volume of a volume of 180,000-525,000 nm$^3$.

For some applications, providing the inner core that includes the phase-change material includes providing an inner core that includes an organic phase-change material.

For some applications, providing the inner core that includes the organic phase-change material includes providing an inner core that includes paraffin.

The present invention will be more fully understood from the following detailed description of embodiments thereof, taken together with the drawings, in which:

DETAILED DESCRIPTION OF EMBODIMENTS

Figure 1A:
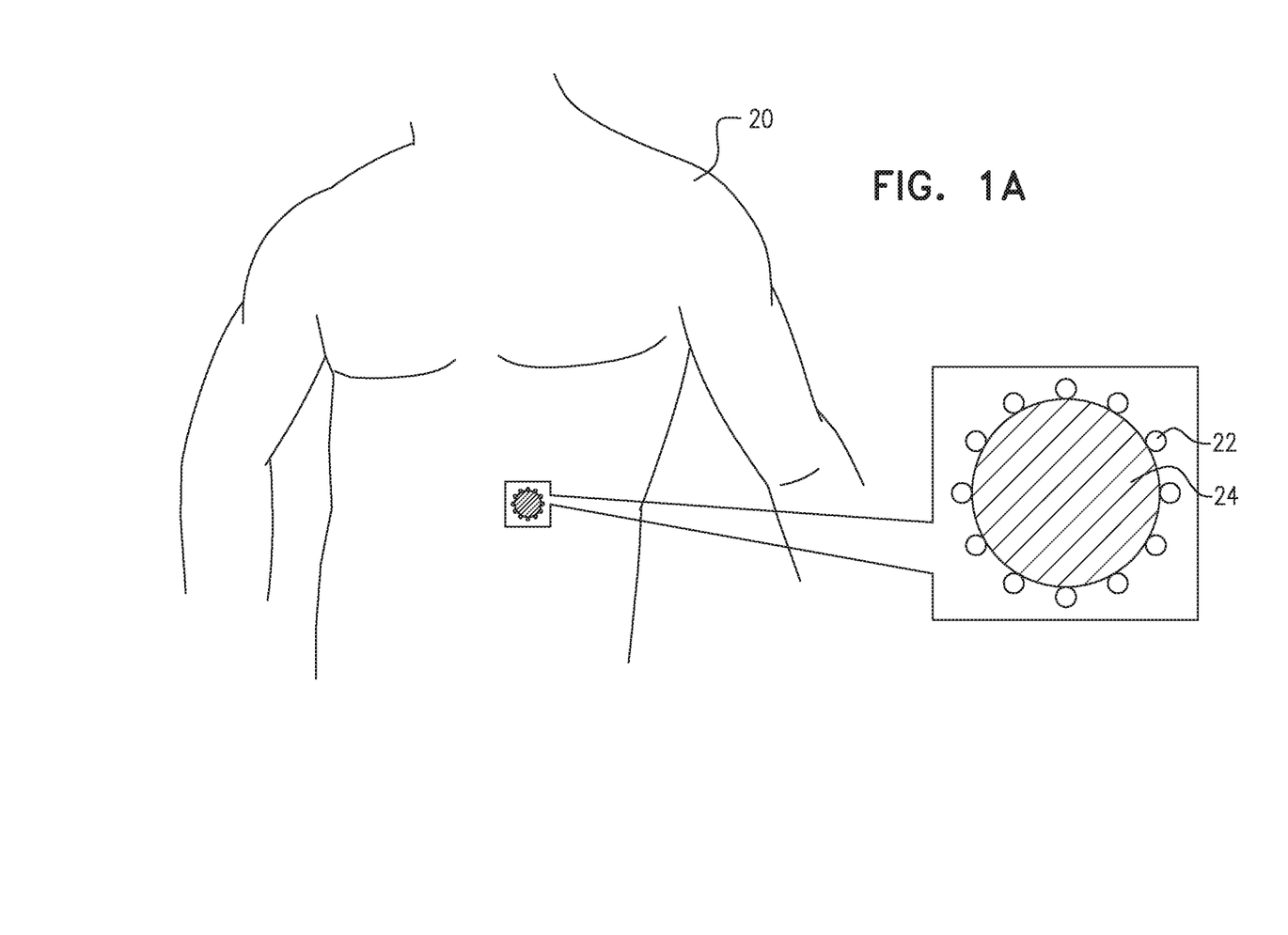
FIGS. 1A-B are schematic illustrations of a subject who is suffering from cancer, a plurality of nanoparticles having been administered to the subject and having become coupled to a tumor that contains cancerous cells, in accordance with some applications of the present invention.
Figure 1B:
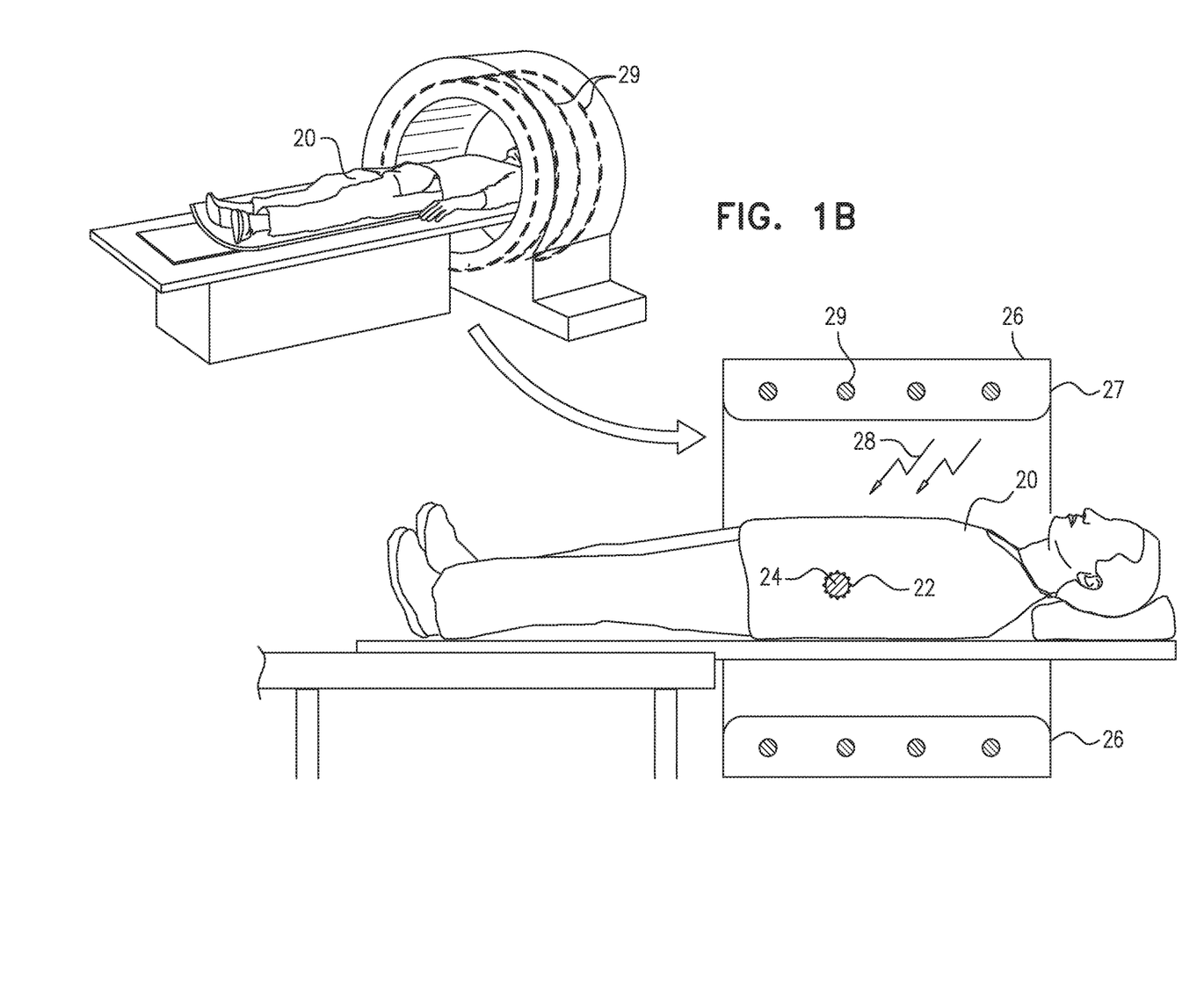

Reference is now made to FIGS. 1A-B, which are schematic illustrations of a subject 20 who is suffering from cancer, a plurality of nanoparticles 22 having been administered to the subject and having amassed at a tumor 24 that contains cancerous cells, in accordance with some applications of the present invention. As shown in FIG. 1B, a heating device 26 is typically used in conjunction with the administration of the nanoparticles to the subject. The heating device transmits energy (schematically illustrated by arrows 28) toward the subject's body, causing at least some of the cancerous cells to become heated, such that the heated cells become injured or ruptured, leading to cell death. The heating device acts as an energy transmission unit.

As described in detail hereinbelow, the nanoparticles typically have the following characteristics:

(1) The nanoparticles preferentially bind to cancerous cells relative to healthy cells.

(2) The nanoparticles preferentially absorb energy transmitted toward the subject's body relative to absorption of the energy by tissue of the subject.

(3) The nanoparticles prevent healthy tissue surrounding the cancerous cells from being heated to a temperature that is greater than a given temperature.

(4) The nanoparticles are at least partially self-adjusting in shape, the nanoparticles being configured to be elongatable to an ellipsoid shape such as to pass through a gap in an anatomical barrier that has a size that is greater than a minimum threshold size, for example, in response to osmotic and/or hydrostatic pressure being exerted on the nanoparticles.

It is noted that typically, the nanoparticles will not become elongated to a precise geometric ellipsoid shape, but will assume a generally ellipsoidal shape when maximally elongated.

For some applications, the heating device 26 with which the nanoparticles are used is an RF-transmitter, which heats the nanoparticles via inductive radiofrequency heating. FIG. 1B shows the patient's body inside the heating device. As shown in the example that is shown in FIG. 1B, heating device (e.g., the RF-transmitter) may include a housing 27 that is shaped like an MRI scanner, such that the entire body of the subject, or an entire potion of the subject's body (e.g., the subject's torso, as shown) is disposed inside the housing. A coil 29 spirals around inside the housing and transmits energy in the general direction of the subject's body.

Alternatively or additionally, heating device 26 may include respective transmission and receiving electrodes (e.g., electrode plates) that are disposed on opposite sides of the subject's body (e.g., above and below the subject's body). For such applications, the heating device is typically configured to generate an electromagnetic field that passes through at least a portion of the subject's body, by transmitting electromagnetic energy from the transmission electrode to the receiving electrode.

Further alternatively or additionally, heating device 26 is shaped differently and/or transmits energy toward the subject's body in a form other than RF energy. For example, the heating device may be housed in a portable housing, and the housing may be sized such that the energy is directed toward a specific portion of the subject's body. The heating device may transmit sonic or ultrasonic energy, and/or may transmit a different range of electromagnetic energy, e.g., optical energy, infrared energy, UV energy, or microwave energy. In accordance with some applications of the invention, the heating device may use Joule heating, magnetic heating, electromagnetic heating, electrophoretic heating, and/or inductive heating.

Figure 2A:
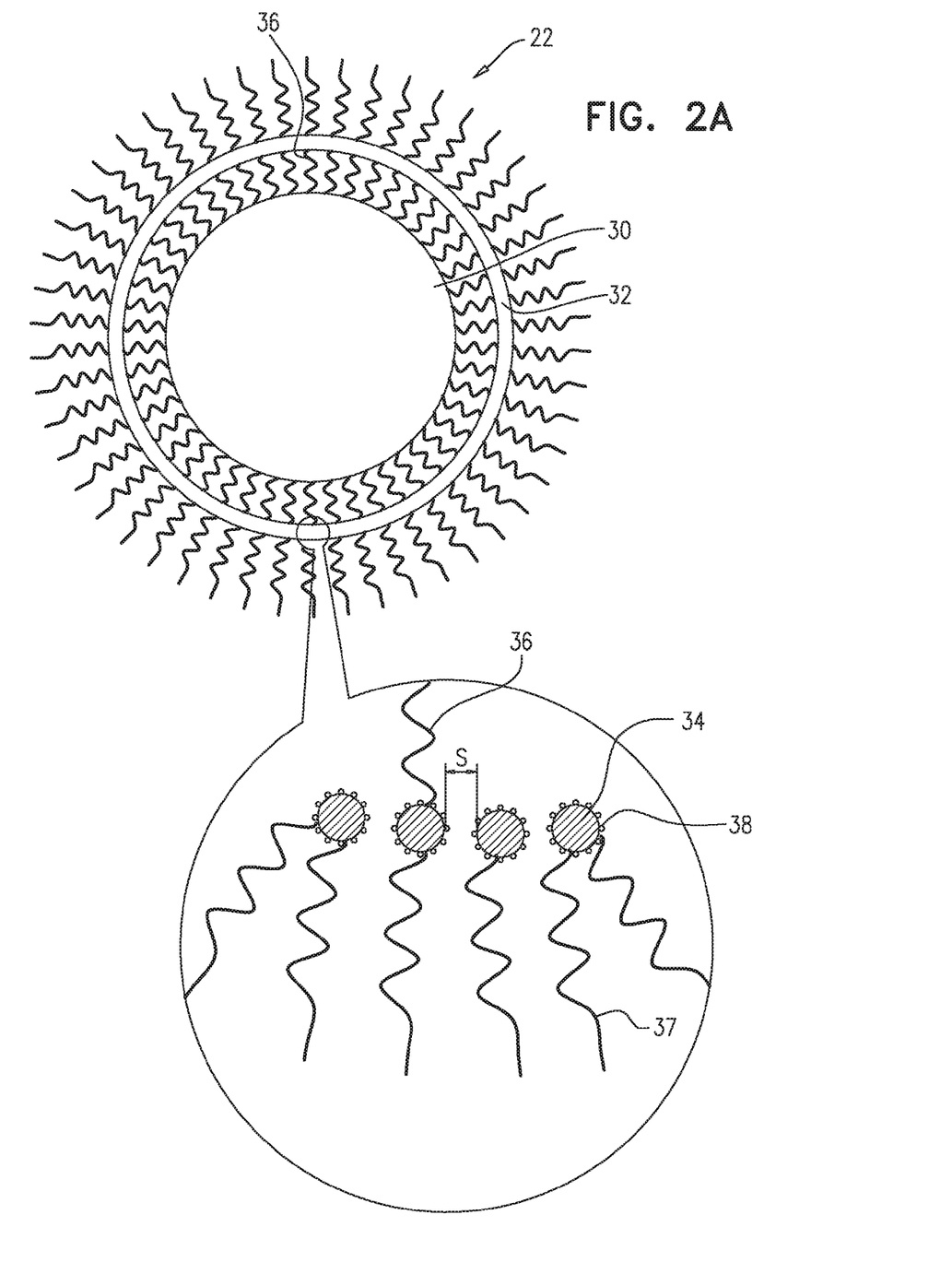
FIG. 2A is a schematic illustration of a cross-section of the nanoparticle, when, as shown for illustrative purposes, the nanoparticle is in a spherical shape, in accordance with some applications of the present invention.
Figure 2B:
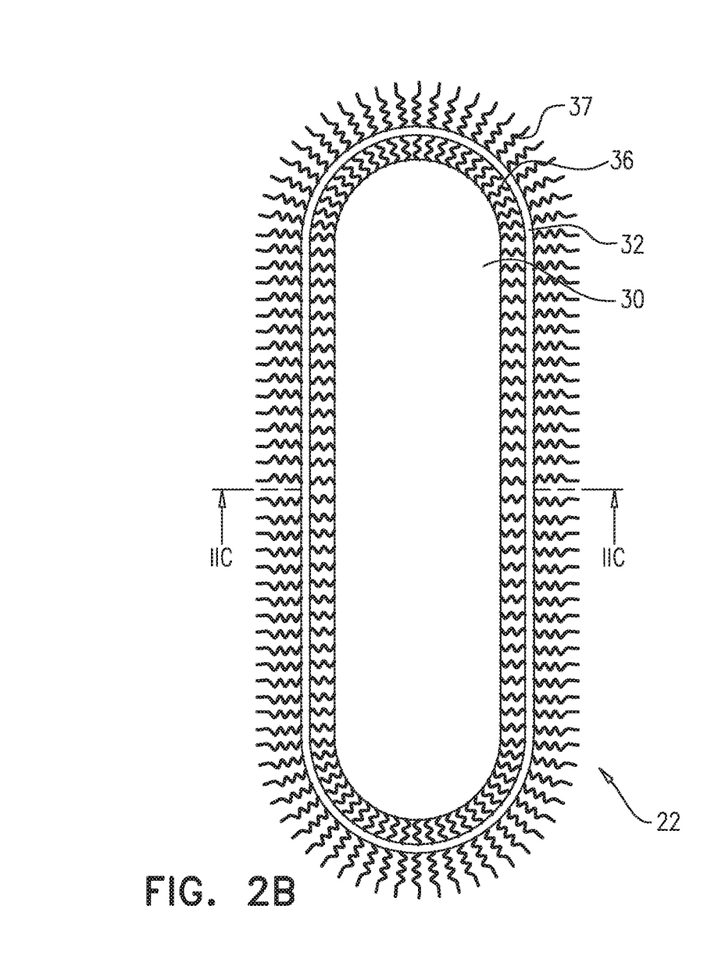
FIGS. 2B-C are schematic illustrations of respective cross-sections of the nanoparticle, while the nanoparticle is in an elongated configuration, in which the nanoparticle is shaped as an ellipsoid, in accordance with some applications of the present invention.
Figure 2C:
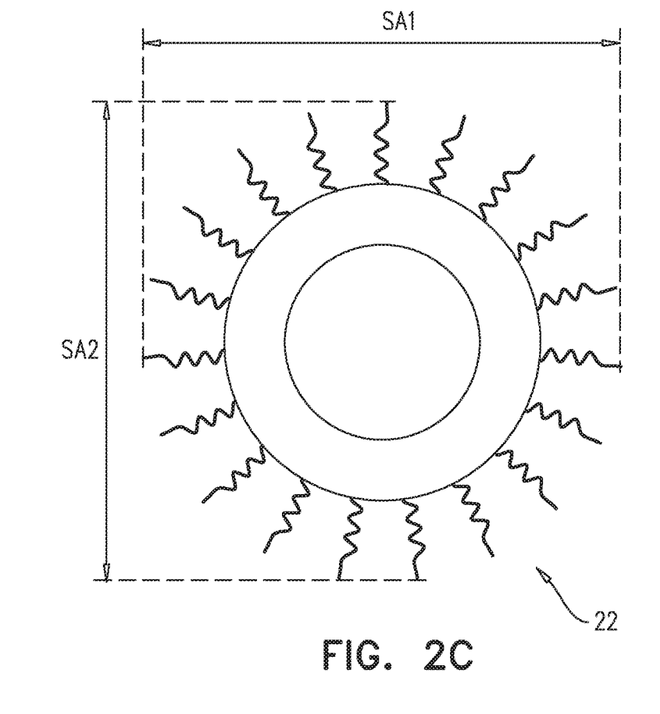

Reference is now made to FIG. 2A, which is a schematic illustration of a cross-section of nanoparticle 22, in accordance with some applications of the present invention. FIG. 2A shows a cross-section of the nanoparticle when the nanoparticle is shaped spherically, for illustrative purposes. Reference is also made to FIGS. 2B and 2C, which are schematic illustration of respective cross-sections of nanoparticle 22, when the nanoparticle is elongated and is shaped as an ellipsoid. It is noted that, for illustrative purposes, the relative dimensions of the respective components of the nanoparticle are not shown to scale in FIGS. 2A-C.

As shown, nanoparticle 22 typically includes an inner core 30 that is a phase-change material. An outer layer 32 is disposed around the inner core, the outer layer including a plurality of nano-spheres 34 of at least one metal. It is noted that the outer layer is typically not a continuous layer, but rather there are separations between each of the nano-spheres and the nano-spheres that are adjacent thereto, as described in further detail hereinbelow. For some applications, polymer chains 36 that define respective hydrophobic and hydrophilic ends are disposed between inner core 30 and outer layer 32, such that the hydrophobic core is bonded to the phase-change material within the inner core, and the hydrophilic ends are bonded to the nano-spheres of the first outer layer. For some applications, polymer chains 37 are disposed around the outside of outer layer 32, as shown.

As shown in the enlarged portion of FIG. 2A, typically, molecules 38 of a substance that binds preferentially with cancerous cells relative to non-cancerous cells are bound to nano-spheres 34. Typically, glucose molecules, and/or molecules of a glucose analog or a glucose derivative (such as fluorodeoxyglucose and/or D-glucose), are used as the substance that binds preferentially with cancerous cells relative to non-cancerous cells. Typically, more than twenty times as many glucose (or glucose analog or glucose derivative) molecules may become coupled to the cancer cells as become coupled to the healthy cells. The preferential uptake of glucose molecules by cancer cells is based on the Warburg effect, described hereinabove in the Background, and as described in "Cancer's Molecular Sweet Tooth and the Warburg Effect," by Kim et al., Cancer Res 2006; 66: (18), Sep. 15, 2006, which is incorporated herein by reference. (The principle of cancer cells preferentially uptaking glucose molecules forms the basis of certain PET-CT imaging protocols.) For some applications, glucose (or a glucose analog or a glucose derivative) is used since glucose is absorbed even into anaerobic tissue, and cancerous tissue is typically anaerobic. Further typically, glucose, glucose analogs, and glucose derivatives bind with both solid tumors and hematological tumors. For some applications, a different type of molecule (e.g., an antibody, a drug, and/or a hormone) that preferentially binds with cancerous cells relative to non-cancerous cells is used.

For some applications, the nanoparticles are administered to the subject systemically (e.g., orally, and/or via intravenous injection), and the nanoparticles are configured to preferentially bind with the cancer cells, by virtue of the fact that the nanoparticle includes the substance that binds preferentially with cancerous cells relative to non-cancerous cells. In this manner the nanoparticles typically amass in the vicinity of a cancerous tumor (e.g., tumor 24, shown in FIG. 1A), and bind with cells of the tumor. For some applications, even in the event that the cancer has metastasized the nanoparticles amass around and bind with metastasized cancer cells.

Typically, outer layer 32 includes a plurality of nano-spheres 34 of at least one metal. Typically, nano-spheres 34 include a noble metal such as ruthenium, rhodium, palladium, silver, osmium, iridium, platinum, and/or gold. For some applications, nano-sphere 34 is a paramagnetic gold superatom nano-sphere. For some applications, an alloy that includes a mixture of two or more metals, or a metal and a nonmetal, is used for nano-spheres 34.

As noted hereinabove, outer layer 32 is typically not a continuous layer, but rather there are separations between each of the nano-spheres and the nano-spheres that are adjacent thereto. Typically, a diameter of each of the nano-spheres is greater than 1 nm (e.g., greater than 3 nm), and/or less than 10 nm (e.g., less than 7 nm), e.g., between 1 and 10 nm, or between 3 nm and 7 nm. Further typically, when nanoparticle 22 is in its spherical configuration (FIG. 2A), a separation S between each of the nano-spheres and an adjacent nano-sphere is greater than 0.3 nm (e.g., greater than 0.5 nm), and/or less than 2 nm (e.g., less than 1.5 nm), e.g., between 0.3 nm and 2 nm, or between 0.5 nm and 1.5 nm. The separation between the nano-spheres allows the nano-spheres to move with respect to each other, which contributes to the nanoparticle having the property of being self-adjusting in shape. By contrast, if outer layer 32 were to be formed as a continuous layer of metal, the outer layer would be relatively rigid. The separation between the nano-spheres is typically not greater than the maximum separation described herein, in order to prevent phagocytic cells of the subject's mononuclear phagocyte system (i.e., the subject's reticuloendothelial system) from penetrating outer layer 32 and breaking down polymer chains 36 and/or the phase-change material of inner core 30.

As described hereinabove, heating device 26 is typically used to transmit energy (e.g., RF energy) toward the subject's body. For example, the heating device may direct inductive radiofrequency heating toward the subject's body (and, therefore, toward the nano-spheres). For some applications, the heating device directs energy toward the subject's body at a resonant frequency of nano-spheres 34, and/or a frequency at which the nano-spheres have high energy absorbance relative to that of the subject's tissue, such that the nano-spheres preferentially absorb energy from the heating device relative to the subject's tissue (e.g., healthy tissue of the subject). The absorption of energy by the nano-spheres is such as to heat the nano-spheres. Since nanoparticles 22 typically amass in the vicinity of cancer cells and bind with the cancer cells, and the nano-spheres preferentially absorb the energy that is transmitted toward the subject, the cancer cells are preferentially heated relative to healthy cells of the subject.

Due to the nanoparticles 22 amassing in the vicinity of cancer cells and binding with the cancer cells, the average heat flux density (i.e., the heat rate per unit area) at the cancer cells within the region of the subject's body that is heated by the heating device is typically substantially greater (e.g., more than twice as great, more than 5 times greater, more than 10 times greater, and/or more than 20 times greater) than that of the average heat flux density at the healthy cells within the region that is heated by the heating device. As a result, the heating of the subject's body (or the portion thereof) by the heating device is typically such as to damage the cancer cells in the subject's body (or in the heated portion) but not to substantially damage the healthy cells therein.

Nanoparticle 22 typically includes inner core 30, which includes a phase-change material. Typically, upon being heated to a phase-change temperature of the phase-change material, the phase-change material is configured to undergo a change of phase from solid to liquid, solid to gel, or gel to liquid. For some applications, the heating device is configured to transmit energy toward the subject's body, such that nanoparticles 22 are heated to the phase-change temperature of the phase-change material. Typically, due to heat being absorbed by the phase-change material as latent heat of fusion, the temperature of the nanoparticles and in the vicinity of the nanoparticles remains substantially constant once the phase-change material has been heated to the phase-change temperature. Further typically, due to heat being absorbed by the phase-change material as latent heat of fusion, the heating device does not heat the cluster to a temperature that is greater than the phase-change temperature.

Typically, the heating device is configured to heat the nanoparticles to the phase change temperature of the nanoparticles, but to prevent heating of the nanoparticles above the phase-change temperature of the nanoparticles, by effecting a phase change of the nanoparticles. For some applications, energy is directed toward the subject's body (or a portion thereof) by the heating device for a period of time that is such that the phase-change material absorbs heat without all of the molecules of the phase change material within inner core 30 changing phase. In this manner, heat continues to be absorbed as latent heat of fusion by the phase-change material within the inner core, throughout the duration of the energy transmission. For example, the heating device may sense a temperature of the clusters using known techniques, and discontinue the transmission of the energy in response to the sensed temperature (e.g., in response to the sensed temperature exceeding the phase-change temperature, which would indicate that heat is no longer being absorbed as latent heat of fusion). Alternatively or additionally, the heating device discontinues transmission of the energy in response to a duration of transmission of the energy, i.e., the unit ceases to transmit energy after a given time period.

For some applications, during treatment of the subject, the heating device transmits energy in an intermittent manner, the unit alternating between ON periods during which energy is transmitted by the unit, and OFF periods during which energy is not transmitted by the unit, or a reduced amount of energy is transmitted by the unit relative to during the ON periods. For some applications, the heating device is configured such that the relative durations of the ON and OFF periods of the unit are such as to heat the nanoparticles to the phase change temperature of the nanoparticles, but to prevent heating of the nanoparticles above the phase-change temperature of the nanoparticles, in the manner described hereinabove.

Typically, the phase-change material is chosen such that the phase-change temperature is a temperature at which the cancer cells will be substantially damaged (e.g., injured or ruptured) but such that the healthy cells in the surrounding tissue will not be substantially damaged. (It is noted that typically some healthy cells may be at least partially damaged.) Since the phase-change material maintains the temperature of the nanoparticles at the phase-change temperature, the heating of the nanoparticles is such as to damage the cancer cells in the vicinity of the nanoparticles but not to substantially damage the healthy cells in the vicinity.

For some applications, the effect of the heating of the nanoparticles on the cancer is in accordance with Table 1, which appears in an article by Thomsen, entitled "Pathologic analysis of photothermal and photomechanical effects of laser-tissue interactions" (*Photochem Photobiol.* 1991 June: 53(6):825-35), which is incorporated herein by reference:

TABLE 1

| Histopathological effect of heating on cells | | | |
|---|---|---|---|
| Thermal damage mechanism | Temperature of onset: range (° C.) | Heating times | Histopathology effect |
| Low-temperature damage accumulation processes | 40-45 | Hours | Reversible cell injury: heat inactivation of enzymes; metabolic acceleration |
| | Low 40+ | Hours to minutes | Edema and hyperemia |
| | 43-45+ | Hours | Cell death: deactivation of enzymes |
| | Unknown | Unknown | Cell shrinkage and hyperchromasia |
| | 43+ | Minutes | Birefringence loss in frozen and thawed myocardium |
| | 45+ | Minutes to seconds | Thermal denaturization of structural proteins in fresh tissue |
| | Unknown 50-90 | Unknown Minutes to seconds | Cell membrane rupture Hyalinization of collagen |
| | 54-78 | 3.6 to 0.4 seconds | Birefringence loss in laser irradiated fresh myocardium |
| | 55-95+ | Minutes | Birefringence changes in collagen |
| Water dominated processes | 100± | Seconds | Extracellular vacuole formation. Rupture of vacuoles, "popcorn" effect |
| | 100-200 | Seconds to milliseconds | Tissue ablation by explosive fragmentation |
| | Over 200 | Seconds to picoseconds | Tissue ablation |

Typically, as stated hereinabove, the region of the subject's body in which cancer cells are located is heated to the phase-change temperature of the phase-change material. For some applications, a phase-change material having a phase-change temperature of more than 42° C. and/or less than 80°

C. (e.g., 42-80° C.) is used. For example, the phase-change material may have a phase-change temperature of more than 42° C. and/or less than 50° C. (e.g., 42-50° C.), more than 50° C. and/or less than 60° C. (e.g., 50-60° C.), or more than 60° C., and/or less than 80° C. (e.g., 60-80° C.).

For some applications, one or more of the phase-change materials that appear in Table 2 and/or in Table 3 (which are extracted from Zalba et al., Applied Thermal Engineering, 23(3), February 2003, pp. 251-283) is used as the phase-change material of inner core 30.

TABLE 2

Melting temperatures of paraffin particles

| Compound | Melting temperature (° C.) | Heat of fusion (Kj/Kg) |
| --- | --- | --- |
| Paraffin C16-C28 | 42-44 | 189 |
| Paraffin C20-C33 | 48-50 | 189 |
| Paraffin C22-C45 | 58-60 | 189 |
| Paraffin wax | 64 | 173.6 |
| Paraffin C28-C50 | 66-68 | 189 |
| Paraffin RT40 | 43 | 181 |
| Paraffin RT50 | 54 | 195 |
| Paraffin RT65 | 64 | 207 |
| Paraffin RT80 | 79 | 209 |
| Paraffin RT90 | 90 | 197 |
| Paraffin RT110 | 112 | 213 |

TABLE 3

Melting temperature of organic phase-change materials:

| Compound | Melting Temperature (° C.) | Heat of Fusion (Kj/Kg) |
| --- | --- | --- |
| Paraffin C14 | 4.5 | 165 |
| Paraffin C15-C16 | 8 | 153 |
| Polyglycol E400 | 8 | 99.6 |
| Dimethyl-sulfoxide (DMS) | 16.5 | 85.7 |
| Paraffin C16-C18 | 20-22 | 152 |
| Polyglycol E600 | 22 | 189 |
| Paraffin C13-C24 | 22-24 | 189 |
| 1-Dodecanol | 26 | 200 |
| Paraffin C18 | 28 | 244 |
| 1-Tetradecanol | 26 | 200 |
| Paraffin C16-C28 | 42-44 | 189 |
| Paraffin C20-C33 | 48-50 | 189 |
| Paraffin C22-C45 | 58-60 | 189 |
| Paraffin Wax | 64 | 173.6 |
| Polyglycol E6000 | 66 | 190 |
| Paraffin C28-C30 | 66-68 | 189 |
| Biphenyl | 71 | 119.2 |
| Propionamide | 79 | 168.2 |
| Naphthalene | 80 | 147.7 |
| Erythritol | 118 | 339.8 |
| HDPE | 100-150 | 200 |
| Trans-1,4-polybutadiene (TPB) | 145 | 144 |

For some applications, one or more of the following organic phase-change materials is used for the phase-change material of inner core 30: crude oil, paraffin produced by the Fischer-Tropsch process, and an organic material having saturated, unsaturated, straight, or branched carbon chain particles. The phase-change material may include, for example, trilaurin, trimyristin, tripalmitin, tristearin, and/or any suitable type of paraffin or paraffin wax.

For some applications, an organic phase-change material is used in inner core 30. For example, paraffin and/or fatty acid particles may be used. For some applications, an organic material is used in inner core 30 because the organic phase-change material freezes without substantial super cooling, is able to melt congruently, has self-nucleating properties, does not segregate, is chemically stable, has a high heat of fusion, and/or for a different reason. For some applications, one or more of the following phase-change materials is used in inner core 30: Octadecane (CAS Number 593-45-3), Lauric acid (CAS No: 143-07-7), Myristic acid (CAS No: 544-63-8), Palmitic acid (CAS No: 57-10-3), Heptadecanoic acid (CAS No: 506-12-7), Stearic acid (CAS No: 57-11-4), Arachidic acid (CAS No: 506-30-9), Behenic acid (Cas No: 112-85-6) Trimethylolethane (CAS No:77-85-0), Stearamine (Octadecylamine) (Sigma-74750), Cetylamine (Hexadecylamine) (Sigma-445312).

In accordance with respective applications of the invention, selection criteria for selecting the phase-change material for use in inner core 30 include thermodynamic, kinetic, and chemical properties of the phase-change material. For some applications, the phase-change material is selected to have given thermodynamic properties, such as a melting temperature in the desired operating temperature range, a high latent heat of fusion per unit volume, high specific heat, high density, high thermal conductivity, small volume changes on phase transformation, small vapor pressure at operating temperatures, and/or congruent melting. For some applications, the phase-change material is selected to have given kinetic properties, such as a high nucleation rate, and/or a high rate of crystal growth. For some applications, the phase-change material is selected to have given chemical properties, such as chemical stability, reversibility of the phase-change cycle without degradation of the particles after a large number of phase-change cycles, non-corrosiveness, and/or non-toxicity.

For some applications, the phase-change material has relatively low thermal conductivity, and is arranged to have a large surface area to overcome the low thermal conductivity and increase the flow of heat into the phase-change material.

As described hereinabove, and as shown in the transition from FIG. 2A to FIG. 2B, typically, nanoparticle 22 is at least partially self-adjusting in shape, the nanoparticles being configured to be elongatable to a generally ellipsoid shape (e.g., a tri-axial ellipsoid shape, or a prolate or oblate ellipsoid of revolution shape). It is noted that typically, the nanoparticle will not become elongated to a precise geometric ellipsoid shape, but will assume a generally ellipsoidal shape when maximally elongated.

Typically, in order for a cancer treatment as described herein to be effective, nanoparticles 22 need to have a certain minimum volume, for at least one of the following reasons:

(1) Tumor cells tend not to bind with particles that are below a given volume.

(2) A minimum volume of nano-spheres 34 of metal is required such as to facilitate preferential absorption of energy by nanoparticles 22. In this manner, the average heat flux density at the cancer cells within the region of the subject's body that is heated by the heating device is substantially greater than that of the average heat flux density at the healthy cells within the region that is heated by the heating device, as described hereinabove.

(3) It is required that the inner core of phase-change material have a given minimum volume, in order for the phase-change material to effectively absorb heat as latent heat of fusion, such as to prevent the temperature of the nanoparticle from rising above the phase-change temperature.

Typically, inner core 30 of the phase-change material has a volume of at least 15,000 $nm^3$, e.g., at least 50,000 $nm^3$, or at least 85,000 $nm^3$. For some applications, inner core 30 of the phase-change material has a volume of less than 400,000 nm³, e.g., less than 270,000 nm³, or less than 145,000 nm³. For example, inner core 30 may have a volume of 15,000-400,000 nm³, e.g., 50,000-270,000 nm³, or 85,000-145,000 nm³.

For some applications, when inner core 30 is shaped spherically (as shown, for illustrative purposes, in FIG. 2A), inner core 30 of the phase-change material has a diameter of at least 30 nm, e.g., at least 45 nm, or at least 55 nm. For some applications, when inner core 30 is shaped spherically, inner core 30 of the phase-change material has a diameter of less than 90 nm, e.g., less than 80 nm, or less than 65 nm. For example, when inner core 30 is shaped spherically, inner core 30 may have a diameter of 30-90 nm, e.g., 45-80 nm, or 55-65 nm.

As described hereinabove, typically, the diameter of each of nano-spheres 34 is greater than 1 nm (e.g., greater than 3 nm), and/or less than 10 nm (e.g., less than 7 nm), e.g., between 1 and 10 nm, or between 3 nm and 7 nm. The length of each of polymer chains 36, when the chain is maximally straightened, is typically greater than 1 nm (e.g., greater than 1.5 nm), and/or less than 4 nm (e.g. less than 3 nm), e.g., 1-4 nm, or 1.5-3 nm. The length of each of polymer chains 37, when the chain is maximally straightened, is typically greater than 2 nm (e.g., greater than 4 nm), and/or less than 10 nm (e.g. less than 8 nm), e.g., 2-10 nm, or 4-8 nm.

Nanoparticle 22 typically has a volume of at least 65,000 nm³, e.g., at least 110,000 nm³, or at least 180,000 nm³. Further typically, in its spherical configuration, the nanoparticle has a diameter of less than 900,000 nm³, e.g., less than 700,000 nm³, or less than 525,000 nm³. For some applications, the nanoparticle has a volume of 65,000-900,000 nm³, e.g., 110,000-700,000 nm³, or 180,000-525,000 nm³.

When it is shaped spherically (as shown, for illustrative purposes, in FIG. 2A), nanoparticle 22 typically has a diameter of at least 50 nm, e.g., at least 60 nm, or at least 70 nm. Further typically, in its spherical shape, the nanoparticle has a diameter of less than 120 nm, e.g., less than 110 nm, or less than 100 nm. For some applications, in its spherical shape, the nanoparticle has a diameter of 50-120 nm, e.g., 60-110 nm, or 70-100 nm. (It is noted that, although the term "nanoparticle" is typically defined as a particle between 1 and 100 nanometers in size, the scope of the present application includes a nanoparticle 22 having a size that is slightly greater than 100 nm, e.g., up to 120 nm, as described.)

It is noted that, solely for illustrative purposes, nanoparticle 22 is shown in FIG. 2A in a spherical configuration, and the dimensions of nanoparticle 22 are provided hereinabove, for when the nanoparticle is shaped spherically. However, nanoparticle 22 does not necessarily assume a spherical shape when in the subject's blood stream, even if the nanoparticle is not being subjected to osmotic, hydrostatic, and/or any other pressure inside the body. Rather, the nanoparticle may assume, for example, a tear shape, a bobble shape, an ellipsoid shape, and/or may be amorphous. However, nanoparticle 22 does have a substantially fixed volume, as provided hereinabove. Furthermore, the nanoparticle is typically configured to be at least partially self-adjusting in shape, such that the nanoparticle is able to pass through an anatomical barrier having a size that is greater than a threshold minimum size, for example, in response to hydrostatic and/or osmotic pressure being exerted on the nanoparticle, as described in further detail hereinbelow.

Typically, the following features of nanoparticle 22 contribute to the nanoparticle being self-adjusting in shape:

1) Inner core 30 is made of a phase change material, such as paraffin, which is amorphous.
2) Nano-spheres 34 are disposed at the end of polymer chains 36 at a separation from one another, such that each of the nano-spheres is able to move with respect to the other nano-spheres.
3) Polymer chains 36 and polymer chains 37 are deformable and may change shape, for example, from a straight line to a coiled configuration.

Typically, nanoparticles 22 are administered to the subject systemically (e.g., orally, and/or intravenously). For some applications, in order to prevent the liver, spleen, glands, and/or any portion of the subject's mononuclear phagocyte system (i.e., the subject's reticuloendothelial system), from filtering the nanoparticles out of the subject's blood, the nanoparticles are configured to elongate (as shown schematically in FIGS. 2B and 2C) into a generally ellipsoid shape, such that at least two of the semi-axes of the ellipsoid have a diameter of less than 30 nm, e.g., less than 25 nm. For example, as shown in FIG. 2C, one of the semi axes of the nanoparticle SA1 is typically less than 30 nm, e.g., less than 25 nm, and a second one of the semi axes of the nanoparticle SA2 is typically less than 30 nm, e.g., less than 25 nm.

For some applications, even in its maximally elongated configuration (i.e., in the configuration in which the nanoparticle is elongated into a generally ellipsoidal shape, but cannot be any further elongated), nanoparticle 22 is configured such that each of the semi axes of the ellipsoid is greater than 5 nm, e.g., greater than 10 nm. For example, as shown in FIG. 2C, both semi axes SA1 and SA2 are greater than 5 nm, e.g., greater than 10 nm. For some applications, in this manner, the nanoparticle is prevented from traversing the blood brain barrier. As described hereinabove, outer layer 32 includes molecules of a substance that binds preferentially with cancerous cells relative to non-cancerous cells. Some of the substances that preferentially bind with cancer cells (e.g., antibodies, glucose, and glucose analogs or derivatives (such as fluorodeoxyglucose and/or D-glucose)) also have preferential uptake by the brain relative to the rest of the body. Therefore, nanoparticle 22 is typically configured such that even in its maximally elongated configuration, each of the semi axes of the ellipsoid is greater than 5 nm, e.g., greater than 10 nm, in order to prevent the nanoparticle from being able to traverse the blood brain barrier.

As described hereinabove, typically, polymer chains 36 define respective hydrophobic and hydrophilic ends, and are disposed between inner core 30 and outer layer 32. Typically, a polyetheramine, e.g., a Jeffamine® polyetheramine, such as polyethylene glycol (PEG) or polypropylene, is used in polymer chains 36. Typically, polymer chains 36 act to bind the inner core 30 to outer layer 32, and contribute to the self-adjusting property of nanoparticle 22 as described herein. Further typically, typically, polymer chains 37 are disposed around outer layer 32. Typically, a polyetheramine, e.g., a Jeffamine® polyetheramine, such as polyethylene glycol (PEG) or polypropylene, is used in polymer chains 37. Polymer chains 37 at least partially mask other components of nanoparticle 22 (e.g., outer layer 32) from phagocytic cells of the subject's mononuclear phagocyte system (i.e., the subject's reticuloendothelial system), thereby preventing the nanoparticle from being broken down by the phagocytic cells.

For some applications, the methods described herein are applied to the subject while imaging the subject, for example, using CT, sonic, ultrasonic, and/or MRI imaging protocols. For some applications, the substance is administered to the subject, and the subject's body (or a region thereof) is irradiated with the energy that is preferentially absorbed by the clusters, as described herein. While the subject's body is irradiated, the subject's body is imaged using a heat-sensitive imaging protocol (for example, using MRI) to detect which regions of the subject's body (including cancer cells) have been heated.

Experimental Data

Nanoparticles including paraffin engulfed with PPO-PEO-PPO/PEO (as generally described hereinabove) were prepared by using an emulsification/solvent evaporation method. Drops of a solution of paraffin wax in dichloromethane were added into an aqueous solution of N,N-Methyl Bisacrylamide (BIS) and a mixture of an acrylated tri/diblock copolymer. Jeffamine® 1900 was used as the tri/diblock copolymer. Jeffamine® 1900 is a block copolymer composed of polypropylene-oxide/polyethylene-oxide: NH2-PPO-PEO-PPO—NH2, functionalized with polymerizable acrylamide groups either (a) at one end, such as to provide a positively charged di-block copolymer of type acryl-NH-A-B—NH3+, or (b) at both ends, such as to provide a tri-block co-polymer of type acryl-NH—B-A-B—NH-acryl.

The mixture was subjected to ultrasonication to form a stable oil-in-water emulsion. Once residual solvent within the droplets was evaporated, nanoparticles of PPO-PEO-PPO/PEO engulfing paraffin wax were obtained, in a nano-reservoir structure. Since the monomers possess polymerizable functions, radical activation at elevated temperature was used to start polymerization and cross-linking within the self-assembled particles, resulting in the formation of nanoparticles with a PEO-PPO-PEO/PEO cross-linked shell structure with an oil-filled core in the interior. The resultant nanoparticles possessed terminal amine groups which acted as attachment points for small colloidal gold particles. The attachment points were used as nucleation sites for the coalescence of a thin gold overlayer using tetrakis(hydroxymethyl)phosphonium chloride (THPC) as a reducing agent. As described hereinabove, the gold nano-spheres were bonded to the nanoparticles, such that each of the gold nano-spheres was separated from all of the other nano-spheres in the overlayer, such that the overlayer formed a segmented shell. The segmented shell thickness was controlled using chloroauric acid and ammonium hydroxide.

SH-PEG2K-Fluorescein isothiocyanate (FITC) was added to 1-Thio-β-D-glucose sodium salt and the mixed solution was added to the encapsulated paraffin nanoparticles. The mixture was vortexed for 10 min and then shaken in an orbital shaker at room temperature for 24 h. The nanoparticles were then centrifuged before being re-dispersed and washed.

Having prepared the nanoparticles in the above-described manner, the nanoparticles were used to perform an experiment on a set of mice. Tumor cells were injected subcutaneously into the set of mice. The volumes of the subcutaneous tumors were measured daily. When the tumor of a given mouse reached 300 mm³ in volume, the mouse was injected with the nanoparticles. The mice were weighed, and a volume of 10 micro-liters of the nanoparticles were injected, per gram of weight of the mouse. After administering the nanoparticles to the mice, the mice were sacrificed at respective times subsequent to the administration of the nanoparticles to the respective mice. Organs, such as the liver and the spleen, of each of the mice were harvested, as was the tumor of each of the mice. The organs, as well as the tumor were weighed, and subsequently, the organs and the tumor were placed in acid, such that all of the organic matter dissolved. The matter that remained from each of the organs and the tumor was then analyzed using inductively coupled plasma mass spectrometry (ICP-MS), in order to detect the amount of gold (from the gold nano-spheres of the nanoparticles) that was present in each of the organs and the tumor. In this manner, the amount of gold per unit weight of tissue was determined for the liver and the spleen, and the tumor. Since, even after being placed in the acid, the gold from the nanoparticles remains intact, the amount of gold present in the organs and tumors of the mice is indicative of the volume of nanoparticles that reached the organs and the tumor.

Figure 3:
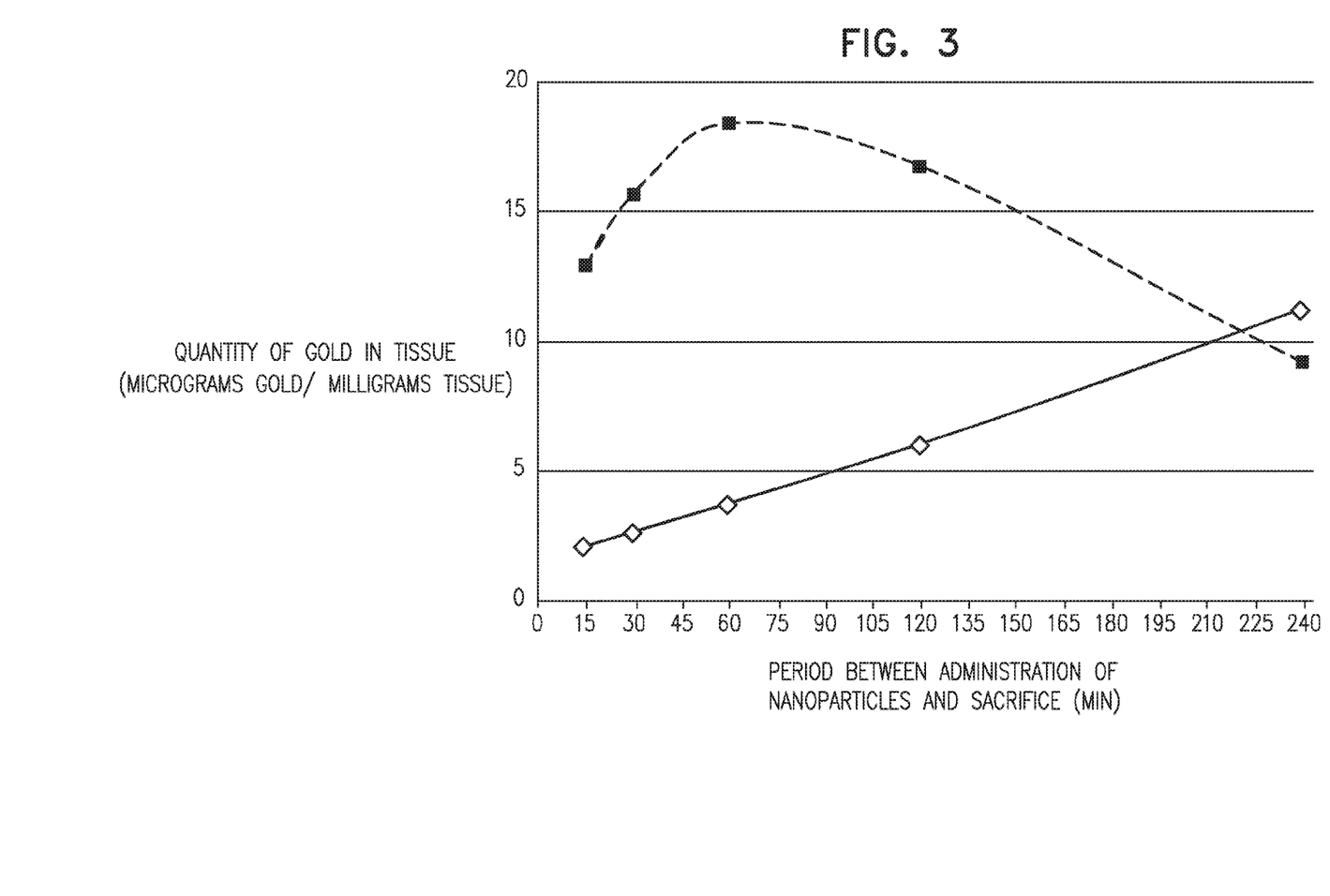
FIG. 3 is a graph showing results of an experiment in which nanoparticles as described herein were administered to mice, in accordance with some applications of the present invention.

FIG. 3 is a graph showing the results of the above-described experiment. The dashed curve shows a plot of the amount of gold (in micrograms of gold, per milligram of tissue) that was present in the livers and the spleens of mice that were sacrificed at respective time periods after administration of the nanoparticles to the mice. The solid line shows a plot of the amount of gold that was present in the tumors of the mice that were sacrificed at the respective time periods after the administration of the nanoparticles to the mice. The graph is based on data from mice that were sacrificed, respectively, 15 minutes, 30 minutes, 60 minutes, 120 minutes, and 240 minutes after the administration of the nanoparticles to the mice.

As stated hereinabove, the amount of gold that was present in the organs and tumors of the mice is representative of the volume of nanoparticles that reached the organs and the tumor. It may be observed that, over time, the amount of gold that is present in the liver and spleen decreases, while the amount of gold that is present in the tumor increases. These results indicate that nanoparticles as described herein (a) are capable of passing through the liver and spleen due the fact that the nanoparticles are self-adjusting in shape, and (b) accumulate in the vicinity of cancerous cells, due to the tendency of the nanoparticles to preferentially bind to cancerous cells.

For some applications, the apparatus and methods described herein are performed in combination with apparatus and methods described in US 2012/0221081 to Hof, which is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   a nanoparticle configured to be administered to a body of a subject, the nanoparticle comprising:
   a phase-change-material layer that comprises a phase-change material that is configured to absorb latent heat of fusion by undergoing a phase change selected from the group consisting of: solid to liquid, and gel to liquid, the phase-change occurring at a phase-change temperature of between 42° C. and 80° C.; and
   an nano-sphere layer disposed around the phase-change-material layer,
   the nano-sphere layer comprising a plurality of nano-spheres of at least one metal,
   the nanoparticle having a volume of at least 65,000 nm³, and
   the nanoparticle being elongatable into an ellipsoid, such that when the nanoparticle is maximally elongated:

each of the semi-axes defined by the ellipsoid is greater than 5 nm, and
at least two of the semi axes of the ellipsoid are less than 30 nm.

2. The apparatus according to claim 1, wherein the nano-sphere layer of the nanoparticle further comprises a plurality of molecules of a substance that binds preferentially with cancerous cells relative to non-cancerous cells.

3. The apparatus according to claim 1, wherein the nanoparticle is configured to become elongated in response to hydrostatic pressure within the subject's body.

4. The apparatus according to claim 1, wherein the nanoparticle is configured to become elongated in response to osmotic pressure within the subject's body.

5. The apparatus according to claim 1, wherein the nanoparticle is configured to be blocked from passing through a blood brain barrier of the subject, by being elongatable into an ellipsoid, such that even when the nanoparticle is maximally elongated, each of the semi-axes defined by the ellipsoid is greater than 5 nm.

6. The apparatus according to claim 1, wherein the nanoparticle is configured to be able to pass through a liver of the subject, by being elongatable into an ellipsoid, such that when the nanoparticle is maximally elongated at least two of the semi axes of the ellipsoid are less than 30 nm.

7. The apparatus according to claim 1, wherein the nanoparticle is configured to be able to pass through glands of the subject, by being elongatable into an ellipsoid, such that when the nanoparticle is maximally elongated at least two of the semi axes of the ellipsoid are less than 30 nm.

8. The apparatus according to claim 1, wherein the nanoparticle is configured to be able to pass through a mononuclear phagocyte system of the subject, by being elongatable into an ellipsoid, such that when the nanoparticle is maximally elongated at least two of the semi axes of the ellipsoid are less than 30 nm.

9. The apparatus according to claim 1, wherein the nanoparticle is configured to be able to pass through a spleen of the subject, by being elongatable into an ellipsoid, such that when the nanoparticle is maximally elongated at least two of the semi axes of the ellipsoid are less than 30 nm.

10. The apparatus according to claim 1, wherein the phase-change material is configured to prevent the nanoparticle from being heated to a temperature that is greater than the phase change temperature, by absorbing latent heat of fusion.

11. The apparatus according to claim 1, wherein the nanoparticle is configured to be used with a heating device that is configured to heat at least a portion of the subject's body, and wherein the nano-spheres of the at least one metal are configured to cause the nanoparticle to preferentially absorb energy from the heating device relative to tissue of the subject.

12. The apparatus according to claim 1, wherein the nano-spheres of the at least one metal comprise gold nano-spheres.

13. The apparatus according to claim 1, wherein the nanoparticle further comprises a plurality of polymer chains disposed between the phase-change-material layer and the nano-sphere layer, the nano-sphere layer being bound to the phase-change-material layer via the polymer chains.

14. The apparatus according to claim 1, wherein each of the nano-spheres has a diameter that is between 1 nm and 10 nm.

15. The apparatus according to claim 1, wherein each of the nano-spheres is separated from all others of the nano-spheres of the nano-sphere layer by a minimum separation of between 0.3 nm and 2 nm.

16. The apparatus according to claim 1, wherein the phase-change-material layer has a volume of 50,000-270,000 $nm^3$.

17. The apparatus according to claim 1, wherein the nanoparticle further comprises a plurality of polymer chains disposed around the nano-sphere layer.

18. The apparatus according to claim 17, wherein the polymer chains are configured to at least partially mask at least the nano-sphere layer from phagocytic cells of a mononuclear phagocyte system of the subject.

19. The apparatus according to claim 1, wherein the nanoparticles are configured to be used with an inductive radiofrequency heating device, and wherein the nano-spheres are configured to be heated by the inductive radiofrequency heating device.

20. The apparatus according to claim 19, wherein the nanoparticles are configured to be used with an inductive radiofrequency heating device that transmits RF energy at a given frequency, and wherein the nano-spheres have a resonant frequency that matches the given frequency.

21. A method for use with a body of a subject, the method comprising:
administering at least one nanoparticle to the subject's body,
the nanoparticle including:
a phase-change-material layer that includes a phase-change material that is configured to absorb latent heat of fusion, by undergoing a phase change selected from the group consisting of: solid to liquid, and gel to liquid, the phase-change occurring at a phase-change temperature of between 42° C. and 80° C., and
a nano-sphere layer disposed around the inner core, the nano-sphere layer including a plurality of nano-spheres of at least one metal, each of the nanoparticles having a volume of at least 65,000 nm3, and
the nanoparticle being elongatable into an ellipsoid, such that when the nanoparticle is maximally elongated:
each of the semi-axes defined by the ellipsoid is greater than 5 nm, and
at least two of the semi axes of the ellipsoid are less than 30 nm; and
subsequent to administering the nanoparticle to the subject, heating at least a portion of the subject's body to the phase-change temperature of the phase-change material, using a heating device.

22. The method according to claim 21, wherein administering the nanoparticle to the subject's body comprises administering the nanoparticle to the subject's body, the nano-sphere layer of the nanoparticle further including a plurality of molecules of a substance that binds preferentially with cancerous cells relative to non-cancerous cells.

23. The method according to claim 21, wherein administering the nanoparticle to the subject's body comprises administering the nanoparticle to the subject's body, the nanoparticle being configured to become elongated in response to hydrostatic pressure within the subject's body.

24. The method according to claim 21, wherein administering the nanoparticle to the subject's body comprises administering the nanoparticle to the subject's body, the nanoparticle being configured to become elongated in response to osmotic pressure within the subject's body.

25. The method according to claim 21, wherein administering the nanoparticle to the subject's body comprises preventing the nanoparticle from passing through a blood brain barrier of the subject's body, due to the nanoparticle being elongatable into an ellipsoid, such that even when the nanoparticle is maximally elongated, each of the semi-axes defined by the ellipsoid is greater than 5 nm.

26. The method according to claim 21, wherein administering the nanoparticle to the subject's body comprises facilitating the nanoparticle passing through glands of the subject, due to the nanoparticle being elongatable into an ellipsoid, such that when the nanoparticle is maximally elongated at least two of the semi axes of the ellipsoid are less than 30 nm.

27. The method according to claim 21, wherein administering the nanoparticle to the subject's body comprises facilitating the nanoparticle passing through a mononuclear phagocyte system of the subject, due to the nanoparticle being elongatable into an ellipsoid, such that when the nanoparticle is maximally elongated at least two of the semi axes of the ellipsoid are less than 30 nm.

28. The method according to claim 21, wherein administering the nanoparticle to the subject's body comprises facilitating the nanoparticle passing through a liver of the subject, due to the nanoparticle being elongatable into an ellipsoid, such that when the nanoparticle is maximally elongated at least two of the semi axes of the ellipsoid are less than 30 nm.

29. The method according to claim 21, wherein administering the nanoparticle to the subject's body comprises facilitating the nanoparticle passing through a spleen of the subject, due to the nanoparticle being elongatable into an ellipsoid, such that when the nanoparticle is maximally elongated at least two of the semi axes of the ellipsoid are less than 30 nm.

30. The method according to claim 21, wherein administering the nanoparticle to the subject's body comprises administering the nanoparticle to the subject's body, the nano-spheres of the metal of the nano-sphere layer of the nanoparticles comprising gold nano-spheres.

\* \* \* \* \*